United States Patent [19]

Castleman

[11] Patent Number: 4,828,800
[45] Date of Patent: May 9, 1989

[54] SYSTEM FOR TRACE GAS DETECTION

[75] Inventor: Bruce W. Castleman, Kenneth City, Fla.

[73] Assignee: Brunswick Corporation, Skokie, Ill.

[21] Appl. No.: 788,659

[22] Filed: Oct. 16, 1985

Related U.S. Application Data

[63] Continuation of Ser. No. 523,478, Aug. 15, 1983, abandoned.

[51] Int. Cl.⁴ ............................................. G01N 1/28
[52] U.S. Cl. ..................................... 422/83; 250/281; 250/282; 422/86; 422/93; 422/98; 436/35; 436/114; 436/119; 436/133; 436/181
[58] Field of Search ................. 250/281, 282; 422/83, 422/98, 93, 86; 436/35, 153, 119, 135, 174, 181, 114, 133

[56] References Cited

U.S. PATENT DOCUMENTS

| | | | |
|---|---|---|---|
| Re. 30,320 | 7/1980 | Lowther | 204/176 |
| 3,540,851 | 11/1970 | Vree et al. | 436/35 X |
| 3,711,251 | 1/1973 | Goodson et al. | 436/153 X |
| 3,725,009 | 4/1973 | Lovelock | 436/153 |
| 3,883,413 | 5/1975 | Douglas-Hamilton | 250/432 X |
| 3,967,933 | 7/1976 | Etess et al. | 422/52 X |
| 3,977,836 | 8/1976 | Matsuda et al. | 422/83 X |
| 4,018,562 | 4/1977 | Parks et al. | 422/52 X |
| 4,091,655 | 5/1978 | French et al. | 250/282 X |
| 4,271,357 | 6/1981 | Bradshaw et al. | 250/282 X |

FOREIGN PATENT DOCUMENTS 1243705  8/1971  United Kingdom ................ 436/153

OTHER PUBLICATIONS

Karels et al; Continuous Method for Sampling Stack Gases for Total Carbon; Environmental Science & Technology, American Chemical Society, 1978, pp. 1046-1051.

Primary Examiner—Robert J. Hill, Jr.
Attorney, Agent, or Firm—Charles G. Mersereau

[57] ABSTRACT

A system for the detection of trace components in a gas by a process involving the ionization of such trace components and intermittently adding to the gas, a reactant gas which converts some of the components to more readily ionizable forms.

4 Claims, 1 Drawing Sheet

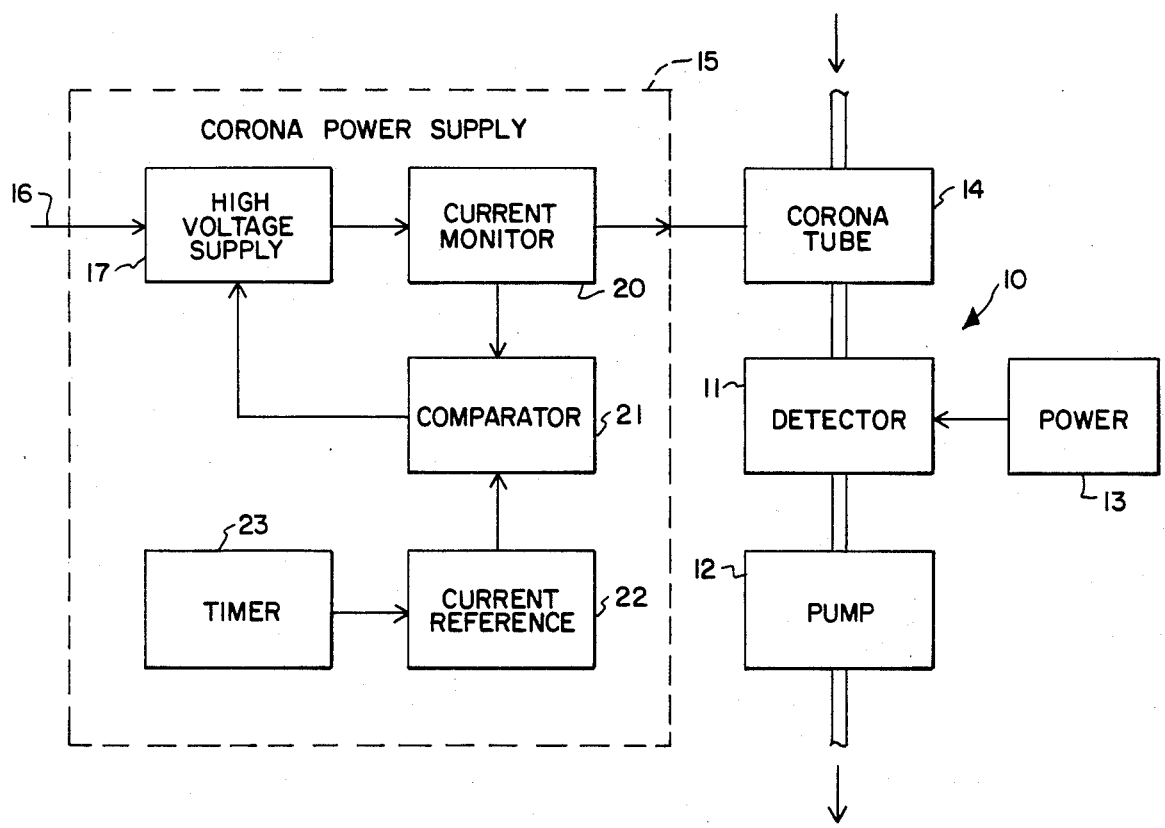

SYSTEM FOR TRACE GAS DETECTION

This application is a continuation of application Ser. No. 523,478, filed Aug. 15, 1983, now abandoned.

FIELD OF THE INVENTION

This invention relates to the field of detection of ions, and more particularly to apparatus and procedures for detecting the presence of gaseous impurities or vapors in low concentration in a carrier gas including air.

BACKGROUND OF THE INVENTION

The detection and identification of trace components of gases and vapors in the atmosphere requires highly sensitive and specific techniques. Examples of such techniques are mass spectroscopy, ion mobility spectroscopy, and ion diffusion techniques. These techniques require that the trace components be ionized or form ion clusters in order to be detected. One apparatus for use in these circumstances is an ionization detection cell shown in U.S. Pat. No. 3,835,328.

It has been found that certain trace components are not easily ionized at atmospheric pressure, particularly in the presence of water vapor, and the sensitivity of the instrument for these substances is low. This can, to some extent, be corrected by a procedure which converts the recalcitrant components to forms, such as oxides, which are more easily ionized, and this can be done by judicious admixture of reactant gases such as ozone. This procedure has the disadvantage, however, that when concentrations of reactant gas are used sufficient to accomplish the desired results with particular trace components, the reactant gas has the effect of partially decomposing other trace components, so that the sensitivity of the apparatus to those other components is actually reduced.

BRIEF DESCRIPTION OF THE INVENTION

The present invention comprises an apparatus for intermittently admixing ozone with a sample gas so that over a time period, the sensitivity of the instrument to various components is modulated, thereby alternately obtaining optimum detection of both types of components.

Various advantages and features of novelty which characterize the invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there is illustrated and described a preferred embodiment of the invention.

BRIEF DESCRIPTION OF THE DRAWING

The single FIGURE of the drawing shows a preferred embodiment of apparatus for practicing the invention.

DESCRIPTION OF THE PREFERRED EMBODIMENT

Apparatus 10 according to the invention is shown to comprise a detector 11 through which the sample gas is drawn by a pump 12. Detector 11 may operate on the basis of mass spectroscopy, gas chromatography, ion mobility spectroscopy, or ion diffusion techniques, and includes apparatus for ionizing the trace components, from a suitable power source 13.

The sample gas is drawn to detector 11 through a source of reactant gas, shown as a corona tube 14 which converts some of the oxygen in the gas to ozone, its reactant form. It is not the function of tube 14 to replace the ionization function in detector 11, but simply to supply ozone for combining with the trace gas components to produce substances which are more readily ionizable in the presence of water vapor, such as sulfoxides of sulfones.

Corona tube 14 is energized from a power supply 15 which will now be described. Energy from a source 16 feeds a high voltage supply 17 which energizes tube 14 through a current monitor 20. A comparator 21 is fed from monitor 20 and a current reference 22 which is subject to a timer 23. By this arrangement, corona tube 14 is supplied with actuating voltage for first periods which alternate with second periods of voltage insufficient to cause ozone generation. The first and second periods are preferably of equal duration, although their lengths may be varied as desired.

OPERATION

Since pump 12 operates continuously, detector 11 is supplied with sample gas which for first intervals includes ozone and for second periods does not include ozone. During the first periods the sensitivity of detector 11 to trace gases such as 2-chloroethylsulfide is increased, while its sensitivity to gases such as dimethylmethylphosphonate is reduced. During the second periods, the sensitivity of the detector to dimethylmethylphosphonate is restored, while its sensitivity to 2-chloroethysulfide is reduced. Over a sufficient interval, detector 11 thus operates at good sensitivity for trace components of both kinds.

From the above it will be evident that the invention comprises an apparatus and a procedure for enhancing the sensitivity, of a detector based on ionization, to trace gases by intermittent admixture of reactant gas such as ozone to intermittently increase the ionizability of certain trace components.

Numerous characteristics and advantages of the invention have been set forth in the foregoing description, together with details of the structure and function of the invention, and the novel features thereof are pointed out in the appended claims. The disclosure, however, is illustrative only, and changes may be made in detail especially in matters of shape, size, and arrangement of parts, within the principle of the invention, to the full extent indicated by the broad general meaning of the terms in which the appended claims are expressed.

I claim:

1. In a system for the substantially continuous detection of a plurality of trace species of interest in a gaseous sample mixture wherein said trace species of interest are of two types, namely, a first type which are readily ionizable and a second type which are recalcitrant or more difficult to ionize, said system comprising detector means including ionization means for ionizing trace species of said first type, detection means for detecting said trace species of interest in the ionized form, and sampling means for causing the continuous flow of said gaseous sample mixture to said detector means, the improvement comprising:

reactant addition means for causing controlled intermittent introduction of a gaseous reactant species into said gaseous sample mixture at a controlled rate and for sequential controlled spaced intervals, said reactant species converting said recalcitrant trace species of said second type into readily ionizable species of said first type during the sequential spaced intervals of introduction of said reactant species;

control means for said reactant addition means including timer means for alternately activating and deactivating said reaction addition means to control the sequential spaced intervals during which said reactant species is introduced in the manner of an on and off cycle basis such that said detector means is able to detect both type one and type two species substantially continually.

2. The apparatus according to claim 1 wherein said reactant species is ozone.

3. The apparatus according to claim 1 further comprising means to modulate the relative amount of reactant species is to produce more accurate results.

4. The apparatus according to claim 1 wherein said reactant addition means further comprises a corona tube and wherein said reactant gas is ozone.

* * * * *